(12) United States Patent
Larsen et al.

(10) Patent No.: US 10,266,499 B2
(45) Date of Patent: Apr. 23, 2019

(54) IMIDAZOLE DERIVATIVES AS PRODRUGS OF DICLOFENAC

(71) Applicant: Claus Selch Larsen, Lejre (DK)

(72) Inventors: Claus Selch Larsen, Lejre (DK); Susan Weng Larsen, Rodovre (DK); Mette Agergaard Thing, Copenhagen (DK); Jesper Langgaard Kristensen, Copenhagen (DK); Henrik Jensen, Roskilde (DK); Jesper Ostergaard, Farum (DK)

( * ) Notice: Subject to any disclaimer, the term of this patent is extended or adjusted under 35 U.S.C. 154(b) by 0 days.

(21) Appl. No.: 15/522,741

(22) PCT Filed: Oct. 27, 2015

(86) PCT No.: PCT/EP2015/074809
§ 371 (c)(1),
(2) Date: Apr. 27, 2017

(87) PCT Pub. No.: WO2016/066612
PCT Pub. Date: May 6, 2016

(65) Prior Publication Data
US 2017/0334862 A1 Nov. 23, 2017

(30) Foreign Application Priority Data
Oct. 28, 2014 (DK) .................. 2014 70657

(51) Int. Cl.
| | |
|---|---|
| A61K 31/4172 | (2006.01) |
| A61K 31/4164 | (2006.01) |
| A61K 31/196 | (2006.01) |
| A61K 31/192 | (2006.01) |
| C07D 233/60 | (2006.01) |
| C07C 229/58 | (2006.01) |
| C07C 229/56 | (2006.01) |
| C07D 233/61 | (2006.01) |
| A61K 45/06 | (2006.01) |

(52) U.S. Cl.
CPC ........ C07D 233/60 (2013.01); A61K 31/4164 (2013.01); A61K 45/06 (2013.01); C07D 233/61 (2013.01)

(58) Field of Classification Search
CPC ............ A61K 31/4172; A61K 31/4164; A61K 31/196; A61K 31/192; C07D 233/60; C07C 229/58; C07C 229/56
USPC .......................... 514/399; 548/341.1, 341.5
See application file for complete search history.

(56) References Cited

U.S. PATENT DOCUMENTS

| | | | |
|---|---|---|---|
| 2014/0315960 A1* | 10/2014 | Larsen ............. | A61K 47/48023 514/357 |
| 2016/0074523 A1* | 3/2016 | Larsen ................. | A61K 31/192 514/357 |

FOREIGN PATENT DOCUMENTS

| | | | | |
|---|---|---|---|---|
| EP | 15787547.7 A1 | 11/2017 | | |
| WO | WO-2013064153 A1 * | 5/2013 | ....... | A61K 47/48023 |

* cited by examiner

Primary Examiner — Matthew P Coughlin
Assistant Examiner — Sagar Patel
(74) Attorney, Agent, or Firm — F. Aaron Dubberley

(57) ABSTRACT

The present invention relates to a compound of formula (I):

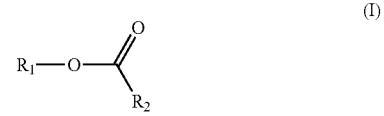

wherein $R_1$ is $R_3$—IPU and $R_2$ is the acyloxy residue of diclofenac,
and specified by the following structures:

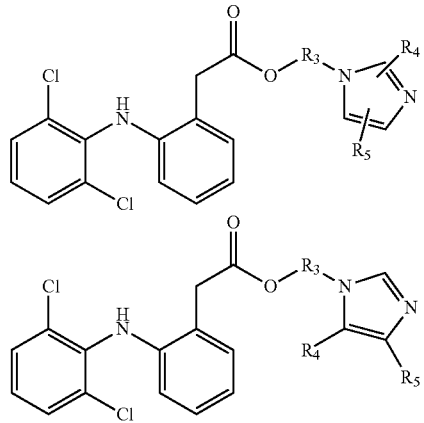

wherein OH—$R_3$—IPU is selected from

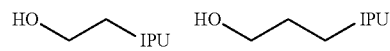

and $R_4$ and $R_5$ may be the same or different selected from H and $CH_3$ and salts, solvates and hydrates thereof.

14 Claims, 7 Drawing Sheets ly at acidic
IMIDAZOLE DERIVATIVES AS PRODRUGS OF DICLOFENAC

FIELD OF THE INVENTION

The present invention relates to novel prodrugs of diclofenac (a specific NSAID) comprising an immobility promoting unit (IPU) covalently linked to diclofenac via a linker, which forms an ester bond. The active pharmaceutical ingredient is diclofenac, an NSAID. The IPU is a substituted or unsubstituted imidazolyl group. It normally has a $pK_a$ value of between 4 and 8.4, between 4 and 7.6 or between 4 and 8.4 including between 7.7 and 8.4 at 37° C. Thus, the novel compounds have a higher solubility at acidic pH compared with neutral or slightly alkaline pH. This difference in solubility at different pH is an important characteristic of the novel compounds as it makes it possible to form a depot of the prodrug in the body after administration as the prodrug is designed to at least partly be present in solid form at the administration site. Thus, the novel compounds are preferably soluble at acidic pH but precipitate at neutral/slightly alkaline pH. Thus, the compounds may be formulated as slightly acidic solutions, but upon injection into a joint the prodrug will precipitate and act as a depot of the drug. In the joint, the prodrug will slowly dissolve and be converted to the active drug substance by hydrolytic enzymes present in the joint. The invention furthermore relates to pharmaceutical compositions of the novel prodrugs, as well as the use of the compounds and compositions as medicaments and for use in specific treatments of i.a. injured and inflamed joints.

BACKGROUND OF THE INVENTION

Modern postoperative pain control focuses on early mobilization and rapid discharge of patients following surgery. Although minimally invasive of nature, arthroscopic procedures do produce pain and inflammation. As a result patients may be prevented from returning to work for weeks after surgery.

Findings have shown that aggressive pain management, including local intra-articular drug therapy, in the early postoperative period can improve convalescence after surgery significantly.

Over the years the efficacy of a significant number of drugs and drug combinations to provide pain relief after intra-articular injection has been investigated. Efficacious intra-articular monotherapeutic approaches include (i) NSAIDs, (ii) local anaesthetics, and (iii) opiates (e.g. morphine). Following arthroscopic procedures promising pain alleviating effects of different intra-articular multimodal analgesic regimens have been reported. Most combinations used consisted of 2-3 drugs selected from opiates, local anaesthetics and anti-inflammatory agents (NSAIDs or corticosteroids) (ref. 1, 2).

Looking to future intra-articular multimodal therapies, particular attention needs to be paid to tailor the duration of action of the individual therapeutic agents whilst keeping the dose of administered compounds to a minimum.

Treatment of e.g. inflammation with NSAIDs is difficult to attain in a site-specific manner. Consequently, a systemic approach is usually employed, where an oral dose is spread through-out the body, thereby limiting the effective dose at the injured or inflamed site, and increasing the emergence of side effects due to high concentrations of NSAIDs in other areas of the body. Attempts to inject the NSAID locally at the site of treatment will only be effective for a few hours, by which time the water-soluble injected drug will, for practical purposes, have diffused out of the joint space, and into the general circulation. This short half-life of intra-articular disappearance of NSAIDs and other small-molecule drugs, which have relatively high water solubility at and around physiological pH, is inhibitive for a continuous release/depot effect.

Simple depot suspensions may be thought to be a preferred way to deliver an immobilised drug since a high drug load can be achieved and minimal pharmaceutical excipients are needed. However, in spite of the relative simplicity of this formulation type compared to more advanced and complex controlled release drug delivery systems, the formulation of (physically) stable injectable suspensions with good shelf-life poses considerable manufacturing challenges.

The problem of administering depot formulations to joints has previously been attempted to be solved by injecting for example suspensions made from steroid esters. Various long-acting steroid ester formulations (aqueous microcrystalline suspensions) are marketed for intra-articular injection. The duration of action of such injectables are 2-6 weeks and thus not indicated for postoperative pain control following minor arthroscopic surgery, which is typically 1-7 days. The drawbacks of using a microcrystalline suspension include that suspensions are difficult to sterilize (e.g. sterilization by filtration is excluded) and that the particle size distribution of the suspended particles may change over time, thereby also changing the in vivo drug release profile. Thus, the formulation of (physically) stable injectable suspensions with good shelf-life poses considerable manufacturing challenges.

Alternatives to microcrystalline depot formulations as described above are injecting a poorly water-soluble salt of the drug solubilised in a co-solvent, which is then precipitated in situ at the injected site (upon contact with water/the biologic fluid, in which the salt is poorly soluble). The drawbacks of this approach is that the release profile is difficult to control—either the release is too fast (1-2 hours) or too slow.

Hydrogels have also been employed, as a possible depot formulation principle. One of the drawbacks of hydrogels is that some do leave behind insoluble residual material in the joint, which is undesirable. Further, a hydrogel does not enable simultaneous release of analgesics (local anaesthetics or opiates over a 24 h period) and anti-inflammatory agents (NSAIDs or corticosteroids over about 7 days), which has been found to improve convalescence after surgery significantly.

There is thus a need in the art for intra-articular depot formulations that may be tailored to have a release profile over 1-10 days.

Further, there is a need for a formulation that does not leave behind insoluble residual material in the joint.

Further, there is a need for a formulation that allows the tailoring of different release profiles in a multimodal regimen.

DESCRIPTION OF THE INVENTION

The present invention was made in view of the prior art described above, and the object of the present invention is to provide novel prodrugs of diclofenac which can be formulated to allow the administered drug to be released over e.g. 1-7 days whilst keeping the dose of administered compounds to a minimum.

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

In general, small-molecule solutes (including NSAIDs) are rapidly cleared from the synovial space after intra-articular (IA) injection. The present invention provides prodrug compounds that has a very low solubility at body pH (i.e. 7.4), which means that the compounds will be in solid or semi-solid form at the administration site. The novel compounds may be injected in the form of a solution (i.e. a slightly acidic solution having a pH of from about 2 to about 5; as described herein the pH is normally dependent on the $pK_a$ of the compound and is from about 2 to about 4 pH units below the $pK_a$ of, the novel compound. If the compounds are administered in the form of a solution, the prodrug compounds form precipitates of low solubility when they are injected into the joint cavity, effectively immobilising the prodrug at the site of required action. The precipitates are in equilibrium with a low concentration of dissolved prodrug (see FIG. 1). The parent drug is regenerated from dissolved prodrug following esterase/hydrolase-mediated cleavage of the prodrug ester bond in the injured or inflamed joint cavity, so releasing the active dissolved drug. However, in some situations the solubility of the prodrugs even at slightly acidic pH may not be sufficient to provide a solution, which can provide a therapeutically effective amount of the compound to the administration site. In such situations it may be necessary to inject the novel compounds in the form of e.g. a dispersion including a suspension or an emulsion. However, preferred novel compounds are those which are soluble at slightly acidic pH optionally in combination with a co-solvent. More specifically the novel compounds preferably have a water solubility at pH 3 and 37° C. of at least 1 microgram/ml, preferably at least 10 microgram/ml and even more preferred at least 25 microgram/ml. Due to the slow dissolution process, therapeutic drug concentrations can be maintained in the joint cavity over relevant and extended periods of time mainly dictated by the free fraction concentration of the prodrug in the inflamed synovial fluid. The prodrug derivatives are designed to have a relatively high solubility in slightly acidic solution but this solubility decreases substantially with increasing pH (up to around physiological pH (about pH 7.4)); the prodrugs are obtained by covalent attachment of water-soluble drug compounds via a linker to appropriate IPUs (immobility-promoting units, such as weak bases containing an imidazolyl functional group with a pKa value in the range of about 4 to about 8.4). Thus, injection of prodrug in the form of slightly acidic aqueous solutions into the joint leads to prodrug precipitation in synovial fluid (in situ precipitate formation). Subsequent availability of the active species is influenced by the rate of dissolution of the precipitate and cleavage of dissolved prodrug by action of hydrolases, including esterases present in the synovial fluid of injured and/or inflamed joints.

Depot drugs of the present invention, which are also referred to as prodrugs, may be useful for monotherapies as well as in multimodal analgesia regimens. The duration of action of the administered medicine will be (roughly) inversely proportional to the rate of dissolution of the precipitated prodrug in the synovial fluid; the rate of dissolution is proportional to the solubility of the prodrug, and this latter parameter can be modified by using IPU's having different physicochemical properties—it is therefore possible to match different IPUs to naproxen or diclofenac as drug compounds in order to achieve a variety of desired release profiles.

To solve the problem the present invention provides a compound of formula (I):

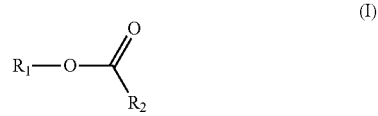

wherein $R_1$ is $R_3$-IPU and IPU is a substituted or unsubstituted imidazolyl group having a molecular weight lower than 1500 g/mol such as lower than 1000 g/mol and a $pK_a$ of between 4 and 8.4 at 37° C.; —O—(C=O)—$R_2$ represents an acyloxy residue of the carboxylic acid group of diclofenac; and pharmaceutically acceptable salts, solvates and hydrates thereof, and salts formed with the same or different NSAID than the NSAID represented by —O—(C=O)—$R_2$.

The function of the IPU is to immobilise the prodrug of formula (I) so that it precipitates/is in solid form when injected into an area containing a bodily fluid at and around physiological pH, but also such that the prodrug of formula (I) is soluble at slightly acidic pH, such as pH 1.5 to 5 for example between pH 2 and 4, such as pH 3 to 4, for example 3.3, 3.5, 3.7 and 37° C.

By modifying the $R_1$ moiety by selecting one or more nitrogen containing moieties, the prodrug of formula (I) can be tailored to precipitate at physiological pH, and be soluble at a pH that is between 2 to 6 units lower, as explained above.

The prodrug of formula (I) is a small molecule drug, which is a low molecular weight organic compound that is not a polymer. By low molecular weight organic compound is considered a compound that has a molecular weight below 600 g/mol, such as 500 g/mol or lower.

More specifically, the novel compounds have a substituted or unsubstituted imidazolyl group as IPU and is covalently linked to diclofenac via a linker such as shown below:

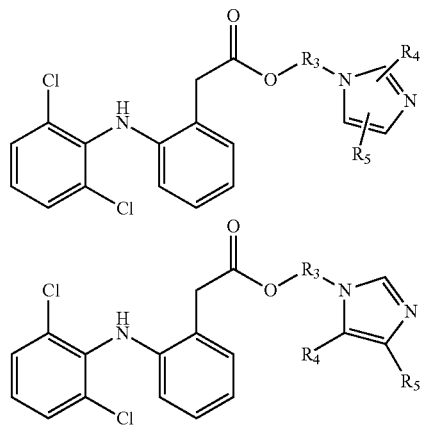

The linker may be linked to a ring carbon atom of the imidazolyl group.

The linker $R_3$ (in the following shown as IPU-$R_3$—OH) may be selected from the following groups:

Thus, the linker may be a straight alkyl having from 2 to 3 carbon atoms. The compounds of the invention include any of the $R_3$ groups shown above (i.e. the IPU indicates the attachment point between $R_3$ and IPU and the —OH group indicates the attachment point to diclofenac.

The imidazolyl group of the IPU has a $pK_a$ value of between 4 and 8.4. It may be selected from substituted or unsubstituted imidazolyl.

The IPU core may contain substituents as indicated by $R_4$ and $R_5$, where $R_4$ and $R_5$ independently of each other are H or $CH_3$.

In general it is preferred that $R_4$ and $R_5$ both are H or at least one of $R_4$ and $R_5$ is H, or at least one or both are $CH_3$. If the $pK_a$ of the imidazolyl group should be modified in order to e.g. adjust the solubility of the prodrug, the imidazole may be substituted with electron donating groups, which increase the $pK_a$ of the imidazole or electron withdrawing groups that decreases the pKa of the imidazole.

The positions of the $R_4$ and $R_5$ substituents are interchangeable.

In the present context, the term "alkyl" designates $C_{1-3}$ alkyl which may be straight or branched, such as ethyl, propyl, and isopropyl.

The imidazolyl group of the novel prodrugs must have a $pK_a$ of between 4 and 8.4 at 37° C. This requirement is important in order to ensure a higher water-solubility at an acidic/slightly acidic pH than at neutral/slightly alkaline pH. To this end, the present inventors have exploited the general knowledge that a certain distance between the N atom and the —O—(C=O)—$R_2$ can be used to avoid an unwanted effect on the $pK_a$ of the amino group. Thus, the N atom of the imidazolyl group and the —O—(C=O)—$R_2$ should be separated by a carbon chain containing two or more carbon atoms.

As mentioned above, the IPU ($R_1$) of the prodrug of formula (I) is an unsubstituted or substituted imidazolyl group. By substitution of the IPU the $pK_a$ can be changed to values of between 4 and 8.4. This may be done by proper manipulation of the moiety by substitution with electron donating groups and/or electron withdrawing groups. Thus, electron donating substituents as alkoxy, phenoxy, amine, and alkyl will increase the pKa of the IPU. Consequently, electron withdrawing substituent as aldehydes, ketones, esters, amides, nitro groups, halogens will lower the pKa. It is well-known to the person skilled in the art to manipulate nitrogen moieties such as for example anilines in this manner to tune the $pK_a$. See for instance the document "*pKa Data Compiled by R. Williams*" (Ref. 3), which can be downloaded from the internet (http://research.chem.psu.edu/brpgroup/pKa_compilation.pdf), and which is the same document that has been cited in the following reference: Caballero et al. (2006) "Theoretical prediction of relative and absolute pKa values of aminopyridines", Biophysical Chemistry 124(2), p 155-160 (Ref. 4).

Specific compounds of the present invention are:

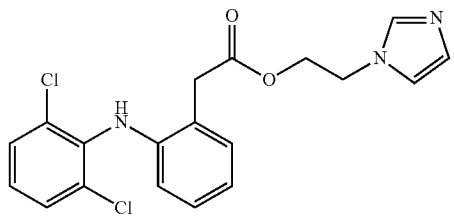

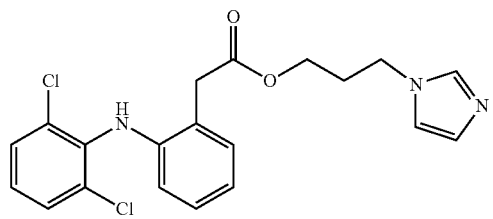

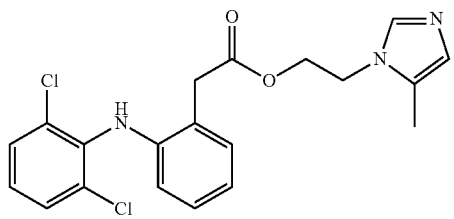

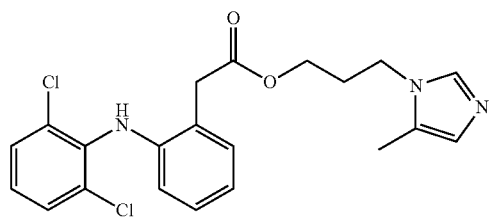

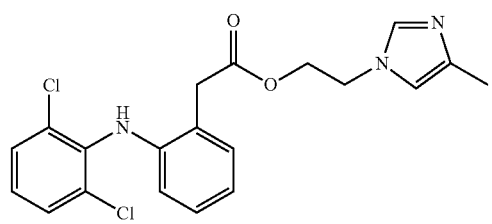

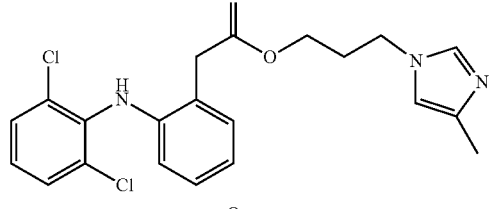

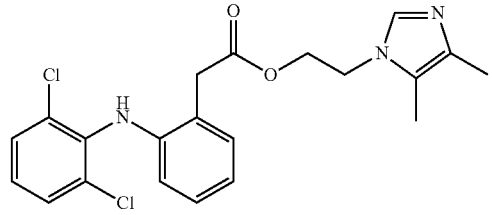

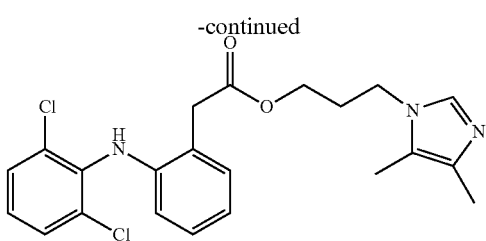

In the formulas above, prodrugs of diclofenac are shown. It is possible to vary:
1) the point of attachment on the Imidazole (see e.g. above)
2) adjust the pKa by varying the substituents on the imidazole (cf above)
3) adjust the solubility of the prodrug by varying the substituents on the imidazole; Increasing the lipophilicity of the IPU will reduce the aqueous solubility of IPU and thus the entire prodrug. If the IPU is substituted with a hydrophilic substituent, the solubility of the IPU and thus the prodrug will increase. Such substituents could be: amines, alcohols, acids, ethers. The nature and length of the linker between the IPU and the NSAID can be used to modify the solubility of the the prodrug. Straight chain aliphatic linkers will reduce the solubility of the prodrug the longer they get. Substitution the linker for a hydrophilic linker like polyethylene glycol will increase the solubility of the entire prodrug.
4) The nature and length of the linker between the IPU and the NSAID can also be used to enable spatial separation between the IPU and the drug to allow the hydrolytic enzyme access to the prodrug bond (minimize steric hindrance);
5) how it is possible to combine the permutations independently of each other.

The present invention offers tailored release of active pharmaceutical ingredients—applicable to monotherapy as well as multimodal regimens—and the possibility to tailor their concomitant release.

In general, the prodrugs of the present invention may have solubility as low as 0.05 µg/ml in 10 mM or 67 mM PBS (phosphate buffer solution) at 37° C. and pH 7.4. In general the solubility is from 0.05 microgram/ml to 1 mg/ml in 10 mM or 67 mM PBS (phosphate buffer solution) at 37° C. and pH 7.4. The increase in solubility is theoretically a factor 500, when the pH is decreased with 3 pH units below the $pK_a$ value of the pro-moiety. However, there may be deviations therefrom. Theoretically, prodrugs with an intrinsic solubility (the saturation solubility of the neutral form of the prodrug) of 100 microgram/ml (37° C.) possess solubilities at pH 7.4 (37° C.) of 101, 110, and 200 microgram/ml in case the $pK_a$ value of the prodrug is 5.4, 6.4, and 7.4, respectively. Likewise, in theory a decrease in pH from 7.4 to 3.0 will increase prodrug solubility by a factor of about 250, 2500, and 12500 in case $pK_a$ of the prodrug is 5.4, 6.4, and 7.4, respectively. Thus, it is important to select prodrugs having suitable balance of $pK_a$ and water solubility at a pH=$pK_a$ in order to obtain the desired dissolution behaviour of the prodrugs at acidic pH and body pH.

The acyloxy residue (—O—(C=O)—R$_2$) is diclofenac belonging to the class of non-steroidal anti-inflammatory agents (NSAIDs.

The prodrug of formula (I) may be formulated as the free base or as a pharmaceutically acceptable salt, or as a solvate or hydrate thereof. By pharmaceutically acceptable salts means those salts of compounds of the invention that are safe and effective for injection in mammals, in particular intra-articular injection, and that possess the desired biological activity. Pharmaceutically acceptable salts include salts of basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, oxalate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate salts. Suitable salts are also those formed with the same NSAID as the one included in the prodrug, i.e. if the prodrug is IPU-linker-diclofenac, then a suitable salt is the diclofenac salt of IPU-linker-diclofenac. Suitable salts are also those formed from another NSAID than the one included in the prodrug, i.e. if the prodrug is IPU-linker-diclofenac, then a suitable salt is e.g. the naproxen salt of the IPU-linker-diclofenac prodrug.

The above-mentioned IPUs may all be linked to diclofenac the resulting structures are all encompassed by the present invention.

Typical ways of making prodrugs of the formula (I) is by esterification of R$_1$(—OH)$_x$ with the corresponding carboxylic acid (HO—(C=O)—R$_2$) of an active pharmaceutical ingredient (API). However, many other ways of preparing prodrugs of formula (I), i.e. containing an IPU linked to one or more API through ester linkage(s). The ester prodrugs were synthesized using two different methods: Reaction of NSAID acid chlorides with IPU-linker-alcohols or coupling of NSAID carboxylic acids with IPU-alcohols using a dehydrating agent as dicyclocarbodiimide (DCC) or 1-ethyl-3-(3-dimethylaminopropyl)-carbodiimide (EDC). Conceivably the prodrugs can also be made from the NSAID carboxylic acid and an alkylation agent under the influence of a suitable base or via acid catalyzed esterification of a NSAID carboxylic acid with and IPU-linker-alcohol.

When the prodrug is soluble, it forms a solution, which is a homogeneous mixture composed of only one phase. When the prodrug precipitates, it forms a heterogeneous mixture composed of a solid phase (e.g. a semi-solid phase) and a liquid phase, where only part of the prodrug is in solution and the rest has precipitated out as a solid (e.g. semi-solid). The solid precipitate may form a crystalline or an amorphous solid.

The prodrugs of the present invention are especially suitable for use in local intra-articular drug therapy.

The solubility of the prodrug of formula (I) at a pH value that is between 2 to 6 units lower than the pH of the physiological fluid it is to be injected into, normally exceeds the corresponding solubility in the physiological fluid it is injected into by at least a factor of 100. Preferably, the solubility is at least 500, such as at least 1000, for example at least 1500 or 2000 times higher than the corresponding solubility in the physiological fluid it is injected into. The physiological fluid may be the synovial fluid, and the volume injected into the synovial fluid may correspond to between 2 and 10% (v/v) or greater of the volume of the synovial fluid. Suitable volumes are normally between 100 µl and up to 2 ml.

A simple way of testing if the solubility is indeed at least 100 times higher than the corresponding solubility in the physiological fluid it is injected into, is to first measure the pH of the physiological fluid that the prodrug of formula (I) is to be injected into. A saturated solution of the prodrug to be measured is made in an aqueous solution at a pH that is between 2 to 6 units lower than the physiological fluid it is to be injected into. Different volumes of this saturated solution is then injected into an aqueous solution at the pH of the physiological fluid that the prodrug is to be injected into, and it is measured if any precipitation occurs, e.g. visually or by other means.

The determination of the solubility of a prodrug at different pH values of interest according to the present invention is carried by adding excess solid prodrug to a container containing a buffer solution with well-defined pH. The mixture is rotated at constant temperature until an equilibrium between solid prodrug and prodrug in solution has established (that is until the prodrug concentration in the supernatant remains constant). At each measurement the pH of the supernatant is controlled and, if needed, adjusted to the desired pH. In a similar manner the solubility of a prodrug in a tissue fluid including the synovial fluid can be determined. The latter procedure comprises a simple way of testing if the solubility at the selected lower pH is indeed at least 100 times higher than the corresponding solubility in the physiological fluid it is injected into. In fact the solubility of DPX-1-0023 amounts to 3019 μg/ml at pH 4.35 whereas the solubility of the prodrug decreases 1118-fold to about 2.7 μg/ml at pH 7.4. For instance, a decrease in pH from pH 7.4 to 2.0 will result in a 1000-fold increase in the solubility of a base with a pKa value of 5, whereas the solubility will increase by a factor of about 9618 for a base with a pKa value of 6. These predicted alterations in pH dependent solubilities can be calculated from the expression: $S_t = S_0 * (1 + 10^{pKa-pH})$ where $S_t$ is the total solubility at a given pH and $S_0$ is the solubility of the neutral form of the prodrug.

Preferably the bodily fluid at physiological pH is synovial fluid, which is found in the synovial cavity of synovial joints. Physiological pH in this case refers to the intra-articular pH of synovial fluid, which may be from pH 6 to pH 8. In cases not involving acidosis the typical values are from pH 7.0 to 7.6, for example between pH 7.2 to 7.5, such as pH 7.3 to 7.45, for example 7.3, 7.35, 7.4.

In another aspect, the invention provides a pharmaceutical composition, which contains a therapeutically effective amount of a compound according to the present invention, and at least one pharmaceutically acceptable carrier, vehicle and/or adjuvant.

The prodrug of formula (I) may be dissolved or dispersed in an aqueous vehicle and the solution or dispersion is made slightly acidic by addition of a calculated amount of an appropriate acid, such as hydrochloric acid to provide a pharmaceutical composition. Such pharmaceutical composition would also be suitable for intra-articular injection. Optionally, a suitable co-solvent might be added to optimize prodrug solubility. Examples of suitable co-solvents are N,N-dimethylacetamide, N-methylpyrrolidone, dimethylsulphoxide (DMSO), polyethylene glycol (PEG 200, PEG 400), propylene glycol, isopropanol, propanol, ethanol and mixtures thereof. In the examples herein a formulation of the prodrugs was provided as a 10 mg/ml suspension ready for use. The suspension contained 0.01% w/v Tween® 80 (polysorbate 80), 0.4% w/v sodium chloride in 67 mM phosphate buffer pH 7.4.

Further, the composition may comprise a dry powder of the prodrug of formula (I) or salt of prodrug to be reconstituted in an appropriate aqueous vehicle just prior to injection.

The particle size of the prodrug, of a powder containing the prodrug or of a suspension of the prodrug is normally as follows (% volume)

D(0.1) from 0.5 to 5 μm, such as from 1 to 3 μm or from 1 to 2 μm
D(0.5) from 7 to 20 μm, such as from 10 to 15 μm or from 11 to 13 μm
D(0.9) from 15 to 40 μm, such as from 20 to 35 μm, from 25 to 30 μm.

As shown in FIGS. 6 and 7 the particle size distribution may show the following (% volume):
D(0.1) from 1.2 to 1.7 μm
D(0.5) from 12 to 13 μm
D(0.9) from 28 to 30 μm.

In some embodiments of the invention, the compounds or pharmaceutical compositions are for use as a medicament, and in other embodiments of the invention, for use in treatment of inflammation in joints, for use in treatment of osteoarthritis and analogous affections. In yet further embodiments the compounds or pharmaceutical compositions are for use in the treatment of postoperative pain following arthroscopic surgery.

The novel compounds and the pharmaceutical compositions of the present invention may be used in medicine such as, e.g. in the treatment of postoperative pain/inflammation following arthroscopic procedures as well as in the management of pain and inflammation in joints or in osteoarthritis associated pain and may accordingly be designed in a form that is suitable for intra-articular injection.

Treating the pathological condition postoperative pain following arthroscopic surgery, involves the treatment of both inflammation and pain, which means that at least one type of API covalently attached via a linker to an IPU with an ester bond is relevant, preferably diclofenac.

In another aspect, the invention provides a method for the preparation of a novel prodrug according to the invention and a method for the preparation of a medicament with anti-inflammatory and pain relieving activity, characterized in that it comprises a prodrug according to the present invention and one or more pharmaceutically acceptable excipients.

Treating the pathological condition inflammation in joints, such as osteoarthritis and analogous affections, involves the treatment of both inflammation and pain which means that at least one type of API covalently attached to an IPU with an ester bond is relevant, preferably diclofenac.

The prodrugs of formula (I) may be used in mammals, preferably humans, horses and dogs.

When describing the embodiments and aspects of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

All particulars and details described herein for the main aspect apply in its entirety to all other aspects.
Other aspect of the invention The prodrugs of the invention may be used in combination with other drug substances to optimize local pain relieving effect e.g. after minor joint surgery.

Modern postoperative pain control focuses on early mobilization and rapid discharge of patients following surgery. Joints are discrete anatomical compartments feasible for local injection of pain alleviating drugs. Although minimally invasive of nature, arthroscopic procedures do produce pain and inflammation. As a result may be prevented from returning to work for up to 2 weeks after surgery. Findings suggest that aggressive pain management (including local IA drug therapies) in the early postoperative period can improve convalescence after arthroscopy. Over the years various IA monotherapeutic approaches have been reasonably effective including nonsteroidal anti-inflammatory drugs (NSAIDs such as diclofenac), local anaesthetics (such as bupivacaine and ropivacaine), and strong analgesics (such as morphine and oxycontin). A reasonable degree of consensus has, however, been reached that total postoperative pain relief is not achievable by use of a single agent or method. Therefore guidelines recommend pain management based on the use of multimodal analgesia approaches wherever possible. Multimodal analgesia involves the use of two or more analgesic drugs differing with respect to mechanism of action. Following arthroscopic procedures promising pain alleviating effects of different IA multimodal analgesic regiments have been reported. Most of the combinations have involved the use of 2-3 drugs selected from the above mentioned groups comprising local anaesthetics, NSAIDs, and opioids. However, in the approached investigated no attention has been paid to the optimization of the duration of action of the individual therapeutic agents. It has been suggested that optimal pain relief after minor joint surgery requires analgesic and anti-inflammatory action locally at the site of trauma over about 1 and 7 days, respectively (for a comprehensive treatise of the subject please see the review by Larsen et al. (2008) J Pharm Sci 97, 4622-4654).

Optimal local pain relieving effect after minor joint surgery has been optimized by use of the NSAID prodrugs of the present invention in combination local anaesthetics such as bupivacaine or ropivacaine in a multimodal analgesic manner where duration of action of the individual therapeutic agents. At completion of surgery marketed injection solutions of the local anaesthetic agent (e.g. Marcain® or Marcain-Adrenalin®) might be injected IA followed by inject of the NSAID prodrug depot injectable. The two injectables might feasibly be purchased as a kit. Alternatively, a slightly acidic injection solution comprising both the local anaesthetic agent and the NSAID prodrug might be administered IA to provide the desired multimodal analgesia. Thus, the prodrugs of the present invention may be used in combined therapy with one of one local anaesthetic agents selected from: amethocaine, chlorprocaine, etidocaine, lidocaine, bupivacaine, mepivacaine, prilocaine, ropivaccine, and procaine.

The prodrugs of the present invention may be used in combined therapy with one or more opioid or strong analgesic selected from: alfentanil, alphaprodine, anileridine, buprenorphine, buturphenol, codeine, dextromoramide, dextropropoxyphene, dihydrocodeine, fentanyl, dydrocodone, hydromorphone, ketobemidone, meptazinol, methadone, morphine, oxycodone, oxymorphone, pentazocine, pethidine, phenazocine, phenoperidine, and sulfentanil.

The drug/prodrugs may be administered in a single composition or in separate compositions e.g. provided as a kit containing two or three containers each containing a composition of i) the prodrug and at least one of ii) a local anaesthetic agent and iii) an opiod. The individual compositions may be combined before administration.

The dosing of the local anaesthetic and/or the opioid for local pain management in connection with arthroscopic joint surgery is well-known to the person skilled in the art.

The invention is illustrated in, but not limited to, the following examples.

EXAMPLES

General procedure for synthesis of compounds according to the invention

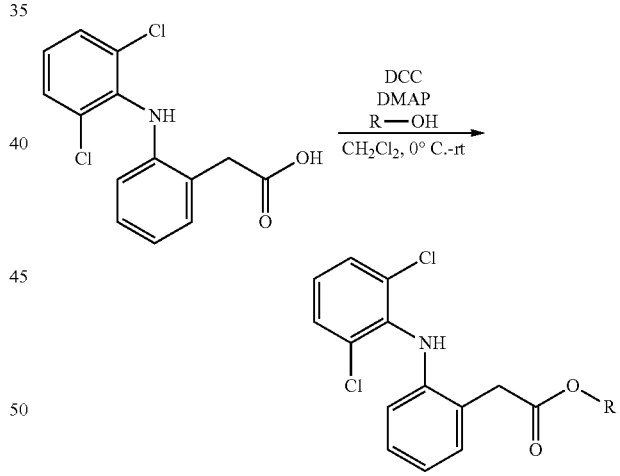

General procedure for the synthesis of prodrugs: Diclofenac free acid (2.96 g, 10 mmol), alcohol (10 mmol) and DMAP (122 mg, 1 mmol) was dissolved in $CH_2Cl_2$ (25 mL) and cooled to 0° C. in an ice-bath. A solution of DCC (4.12 g, 20 mmol) in $CH_2Cl_2$ (25 mL) was added dropwise over the course of 30 minutes. After complete addition the reaction was allowed to reach room temperature over 3 hrs. The reaction was filtered and the filtrate was evaporated to give a pale yellow oil which was purified by flash chromatography (0-10% 2M methanolic $NH_3$ in EtOAc) to give the desired ester.

Example 1

Synthesis of DPX-1-0018

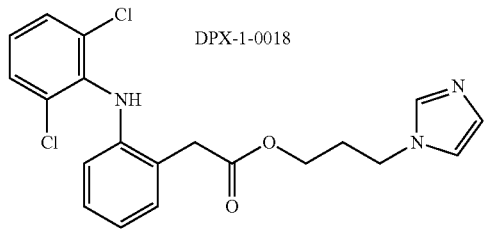

DPX-1-0018

Chemical Formula: $C_{20}H_{19}Cl_2N_3O_2$
Molecular Weight: 404,29

Prepared from 4-(1H-imidazol-1-yl)butan-1-ol by general procedure A in 70% yield. The free base was dissolved in EtOH (0.1 g/mL) and treated with 1.2 equiv. of PhSO3H in EtOH. Dilution with Et2O resulted in precipitation of crystals which was isolated by filtration to give the besylate salt as colorless crystals.

Characterization of DPX-1-0018

2.1 1H NMR Data

1H NMR (600 MHz, CDCl3) δ 7.46 (s, 1H), 7.28 (d, J=8.1 Hz, 2H), 7.15 (dd, J=7.6, 1.5 Hz, 1H), 7.06 (td, J=7.8, 1.5 Hz, 1H), 6.99 (s, 1H), 6.92 (t, J=8.1 Hz, 1H), 6.88 (td, J=7.4, 1.0 Hz, 1H), 6.78 (s, 1H), 6.75 (s, 1H), 6.48 (d, J=8.0 Hz, 1H), 4.10 (t, J=6.4 Hz, 2H), 3.85 (t, J=7.1 Hz, 2H), 3.74 (s, 2H), 1.78-1.70 (m, 2H), 1.62-1.54 (m, 2H). 13C NMR (151 MHz, CDCl3) δ 172.4, 142.8 (2C), 137.8, 137.0, 131.0, 129.7, 129.1 (3C), 128.3, 124.3 (2C), 122.2, 118.9, 118.4, 64.4, 46.8, 38.8, 27.7, 25.8.

2.2 XRPD

Figure 1:
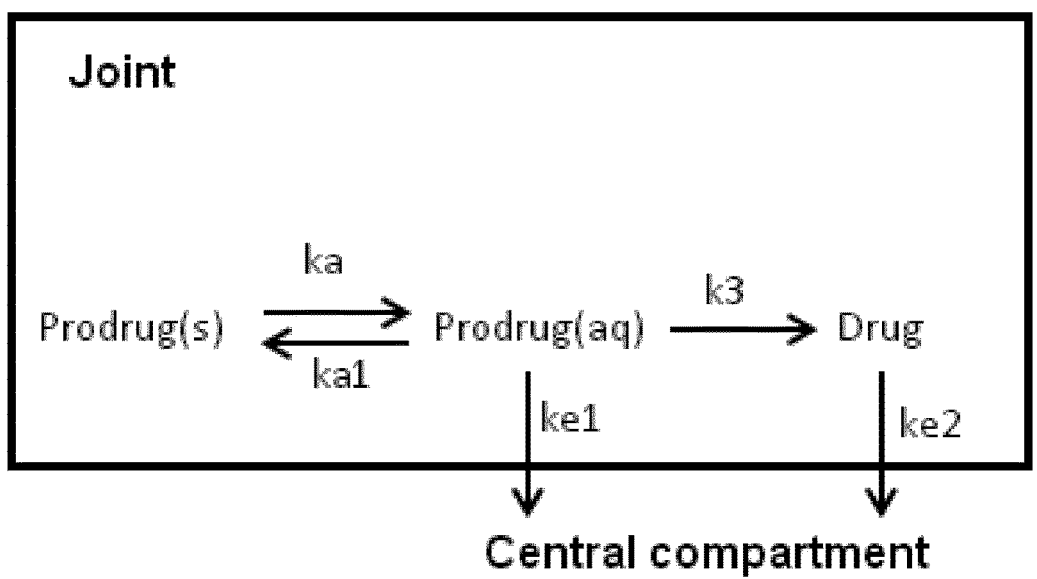
FIG. 1 shows factors influencing the pharmacokinetic fate of the prodrug/drug after administration of the prodrug into the joint. The prodrug dissolved is converted into the active drug by enzymatic cleavage of the prodrug bond.
Figure 2:
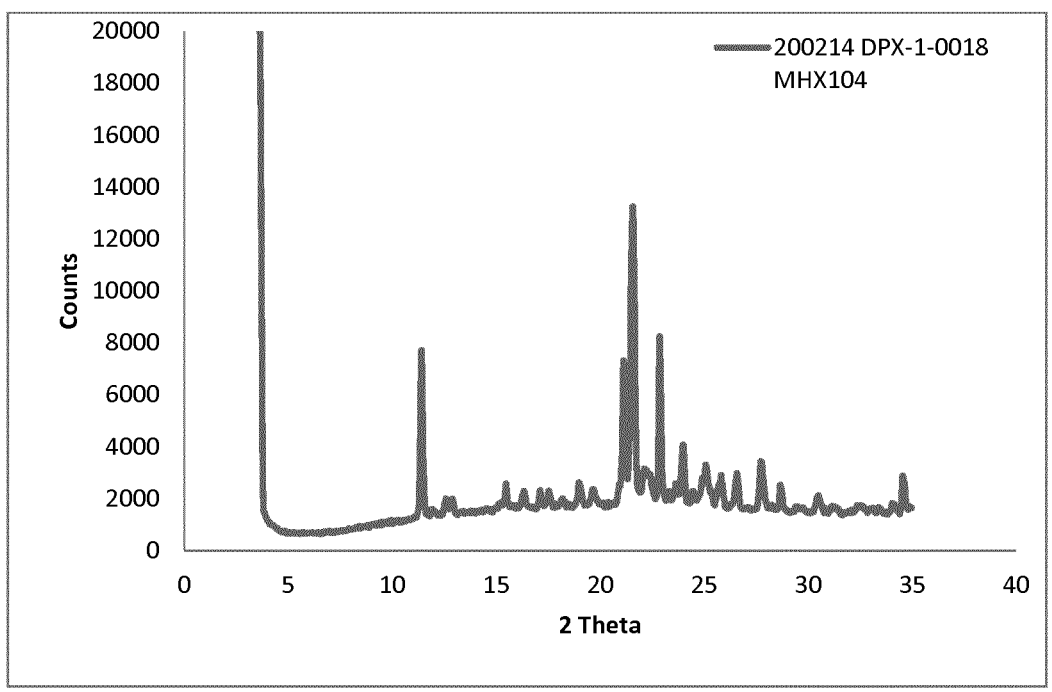
FIG. 2 shows the X-ray powder diffraction diagram of PPX-1-0018.

Crystalilne—see FIG. 2.

Example 2

Synthesis of DPX-1-0023

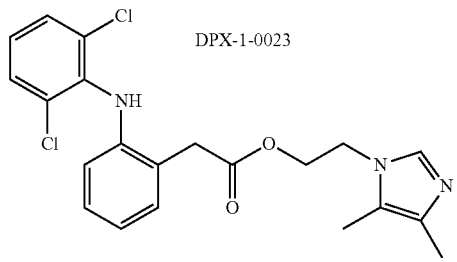

DPX-1-0023

Chemical Formula: $C_{21}H_{21}Cl_2N_3O_2$
Molecular Weight: 418,32

DPX-1-0023 is prepared from 2-(4,5-dimethyl-1H-imidazol-1-yl)ethanol by general procedure A in 75% yield.

Characterization of DPX-1-0023

The compound is obtained in the base form.

2.2 NMR Data

1H NMR (free base, 600 MHz, CDCl3) δ 7.28 (s, 1H), 7.27 (d, J=8.1 Hz, 2H), 7.12 (d, J=7.5 Hz, 1H), 7.07 (t, J=7.7 Hz, 1H), 6.92 (t, J=8.1 Hz, 1H), 6.90 (t, J=7.6 Hz), 6.63 (s, 1H), 6.48 (d, J=8.0 Hz, 1H), 4.26 (t, J=5.6 Hz, 2H), 4.00 (t, J=5.6 Hz, 2H), 3.74 (s, 2H), 2.07 (s, 3H), 2.03 (s, 3H). 13C NMR (free base, 150 MHz, CDCl3) δ 172.1, 142.8 (2C), 137.8, 135.3, 133.9, 131.1, 129.6, 129.0 (2C), 128.4, 124.3, 123.9, 122.4, 122.1, 118.5, 63.8, 43.6, 38.5, 12.7, 8.5.

2.3 XRPD

Figure 3:
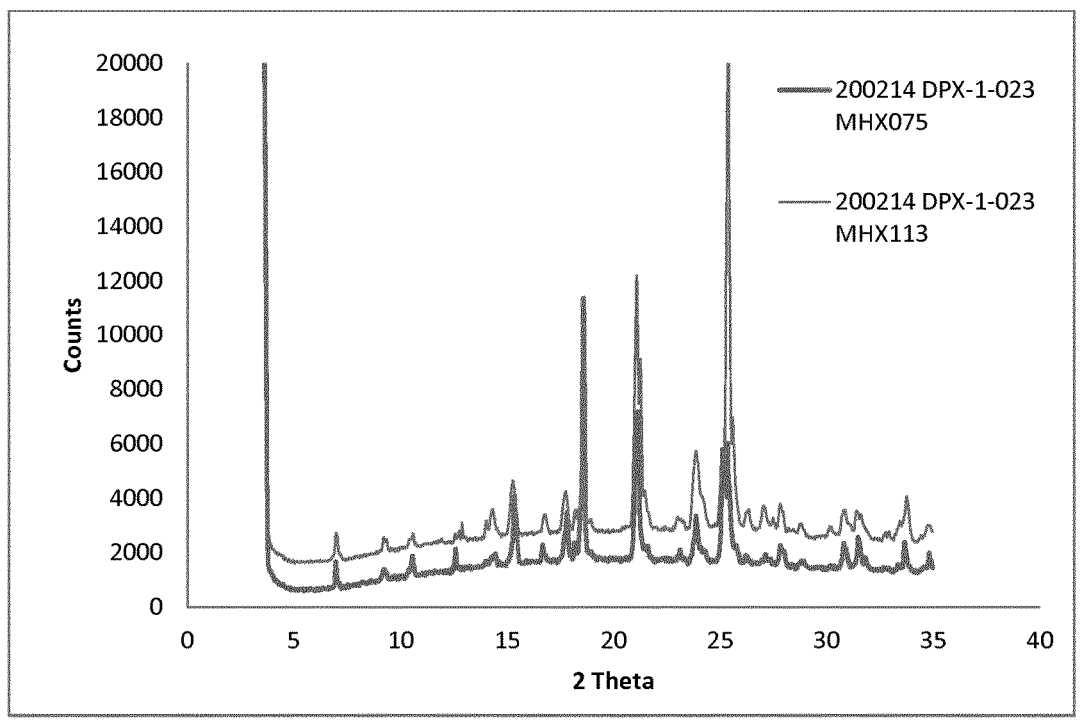
FIG. 3 shows the X-ray powder diffraction diagram of PPX-1-0023.

Crystalline-see FIG. 3.

2.4 Melting Point (DSC), CHN-Analysis and TGA

| Batch | Form | MP (DSC) |
| --- | --- | --- |
| MHX075 | base | 129.3 |
| MHX113 | base | 129.2 |

2.5 pKa-Value

The pKa-value for DPX-1-0023 at 25° C. using a GLpKa meter was found to 7.92.

2.6 HPLC Analysis

HPLC System A

Samples were analyzed on an Elite LaChrom HPLC system (VWR International, Tokyo, Japan) employing a Merck-Hitachi L-2130 pump connected to a Merck Hitatchi L-2450 diode array detector and a VWR-Hitachi L-2200 autosampler. Reversed phase chromatography was performed using a Gemini C18 column (150×4.60 mm; 5 µm particles, Phenomenex, Allerød, Denmark) equipped with a Gemini C18 precolumn (4×3.0 mm, Phenomenex, Allerød, Denmark) heated at 30° C. by a VWR Hitachi L-2300 column oven. The mobile phase consisted of methanol and 0.02 M acetate buffer pH 4.4 in ratio (v/v) of 65:35. The flow rate was set at 1 ml/min and the column effluent was monitored at 275 nm. Retention time 3.9 min for DPX-1-0023, 8.0 min for diclofenac.

The retention time is strongly dependent on pH and thus changes must be expected between batches of mobile phases and also the matrix the prodrug is dissolved in.

2.7 Solubility

A surplus of prodrug was added to either PBS pH 7.4 or $H_2O$. 0.1 M HCl was added to the $H_2O$ to decrease pH to around 3-4. The mixtures were rotated at 37° C. and a sample was withdrawn after approximately 24 and 48 hours or later. The withdrawn sample was filtered through a 0.45 µm Millex®-HV (Millipore, Japan) low protein binding filter (the first 0.5 mL discarded) and a known volume of the sample was diluted. The pH 7.4 samples were diluted with PBS and the acidic samples with mobile phase A (section 2.5). A standard dissolved in PBS was made for the pH 7.4 samples and a standard dissolved in mobile phase A for the acidic samples. The PBS standards used for the standard curves were treated like the samples to avoid false results caused by adsorption. The standard curves were made to cover the concentration interval of the samples after dilution.

From the observed relatively stable concentration of dissolved prodrugs measured in the suspensions after 8-9 day up to 23 days, the solubilities of the prodrugs ($S_{prodrug}$) were determined. In this time interval, the rate of appearance of parent drug was determined and an apparent pseudo-zero-order rate constant ($k_0$) was obtained. By assuming that the dissolution rates were much faster than the conversion of the prodrugs to the parent drug, pseudo first-order rate constants ($k_{hyd}$) for cleavage of the prodrugs were calculated according to:

$$-\frac{d[Prodrug]}{dt} = \frac{d[Drug]}{dt} = k_{hyd}S_{prodrug} = k_0$$

All data are summarized in Table 1.

TABLE 1

Solubilities of DPX-1-0023 in 67 mM phosphate buffer pH 7.4 and in hydrochloride solutions at pH 4.35 at 37° C. n = 6 (equal solubilities were obtained after 1 and 2 days of rotation).

| pH | S (µg/ml) | S (mM) |
|---|---|---|
| 4.35 | 3019 ± 62 | 7.2 ± 0.1 |
| 7.4 | 2.7 ± 0.2 | 0.0064 ± 0.0005 |

2.8 Stability

Stability in PBS 7.4, 80% (v/v) Plasma, 80% (v/v) SF and 80% (v/v) Rat Serum

The stability of the prodrugs was determined in PBS, 80% human SF, 80% human plasma and 80% rat serum at 37° C. 10, 20 or 50 µL of prodrug solution in MeOH was added to 1.0 mL 80% rat serum, 2.5 mL 80% SF or human plasma or 10.0 mL PBS, respectively to give a final prodrug concentration corresponding to the solubility at pH 7.4 at 37° C. Samples were withdrawn at appropriate intervals depending on the rate of degradation. The samples from the biological medias were added to MeCN (1:2 (v:v)) vortexed and centrifuged (5 min, 10000 RPM) and the supernatant analyzed by HPLC. The 700 µL PBS samples were added to 100 µL PBS and mixed before analysis by HPLC. First a pilot study was performed with n=1 to find the appropriate sampling times and thereafter an experiment with n=3. The stability was determined from the decrease in the area of prodrug.

TABLE 2

Half-lifes of DPX-1-0023 in 80% plasma, spinal fluid (SF), rat serum and phosphate buffer solution (PBS) at 37° C.

| | Plasma | SF batch 210513 | Rat serum | PBS |
|---|---|---|---|---|
| $T_{1/2}$ (min) | 5.1 ± 0.5 | 39.8 ± 2.8 | 6.1 ± 0.4 | 1083 ± 164 (0.75 days) |

The data reveal that that the prodrug is much instable in the 3 biological media (same pH as PBS) as compared with the stability in PBS. Thus, in the 3 biological media, prodrug cleavage to yield active diclofenac involves catalysis by hydrolytic enzymes present in these matrices.

Example 3

Animal studies

The aim of the animal study is given in the following.

Osteoarthritis is the most common form of joint disease. Nearly one third of adults in the United States suffer from osteoarthritis and it is the most common cause of disability in adults in the United States. The monosodium iodoacetate (MIA) model of osteoarthritis described here produces changes in the structure and integrity of the affected cartilage that is very similar to what is seen in human osteoarthritis. Sodium iodoacetate is a metabolic inhibitor that, when injected into the joint space, selectively kills chondrocytes, the cells that form cartilage. Over a period of 2-3 weeks, the loss of cartilage produces a state highly analogous to human osteoarthritis characterized by joint instability, loss of cartilage, and decreased bone quality around the affected joint. These physiological changes are also accompanied by pain in the affected joint.

In this study, osteoarthritis was induced by a single injection of MIA (2 mg) into the synovium of the left knee, which results in increased sensitivity to pressure. For this particular study, the test compounds were given 14 days post-MIA injection to determine if the test compound can reduce the sensitivity.

Study design

Vehicle (0.01% Tween 80 in phosphate buffer) administered intra-articularly at a dose volume of 30 µl on day 0.

Test articles DPX-1-0008, DPX-1-0011, DPX-1-0018, DPX-1-0020, DPX-1-0023, and DPX-1-0024, administered intra-articularly at a dose of 0.3 mg on day 0.

Diclofenac, administered orally at a dose of 10 mg/kg on day 8 to the vehicle group.

Methods

A total of 82 male, Sprague-Dawley rats underwent MIA injection with the goal of having 70 animals available for the pharmacology treatment due to 15% failure of developing a pain state. Fourteen days after MIA injection, animals met the inclusion criteria were assigned to one of seven groups (vehicle, test article DPX-1-0008, DPX-1-0011, DPX-1-0018, DPX-1-0020, DPX-1-0023, and DPX-1-0024) and received the assigned treatment. Joint compression thresholds were assessed prior to MIA injection, prior to dosing with control/test articles, and 1, 2, 4, and 7 days post-dosing. Diclofenac served as the positive control for the study. On day 8, animals in the vehicle group received diclofenac (10 mg/kg, PO) and joint compression were assessed prior to, 1 and 2 hours after dosing for all the animals. All animals were euthanized on day 8 following the behavioral assessment.

Results

Injection of 2 mg MIA into the knee significantly decreased joint compression thresholds 14 days after injection. Intra-articular administration of DPX-1-0018 (0.3 mg) significantly increased mean joint compression thresholds 8 days post-dosing compared to the vehicle group. Intra-articular administration of DPX-1-0020 (0.3 mg) significantly increased mean joint compression thresholds 8 days post-dosing compared to the vehicle group. Intra-articular administration of DPX-1-0023 (0.3 mg) significantly increased mean joint compression thresholds 1 day post-dosing compared to the vehicle group.

Oral administration of the positive control, diclofenac (10 mg/kg), significantly increased mean joint compression thresholds 1 and 2 hours post-dosing compared to baseline values on day 8.

Figure 4:
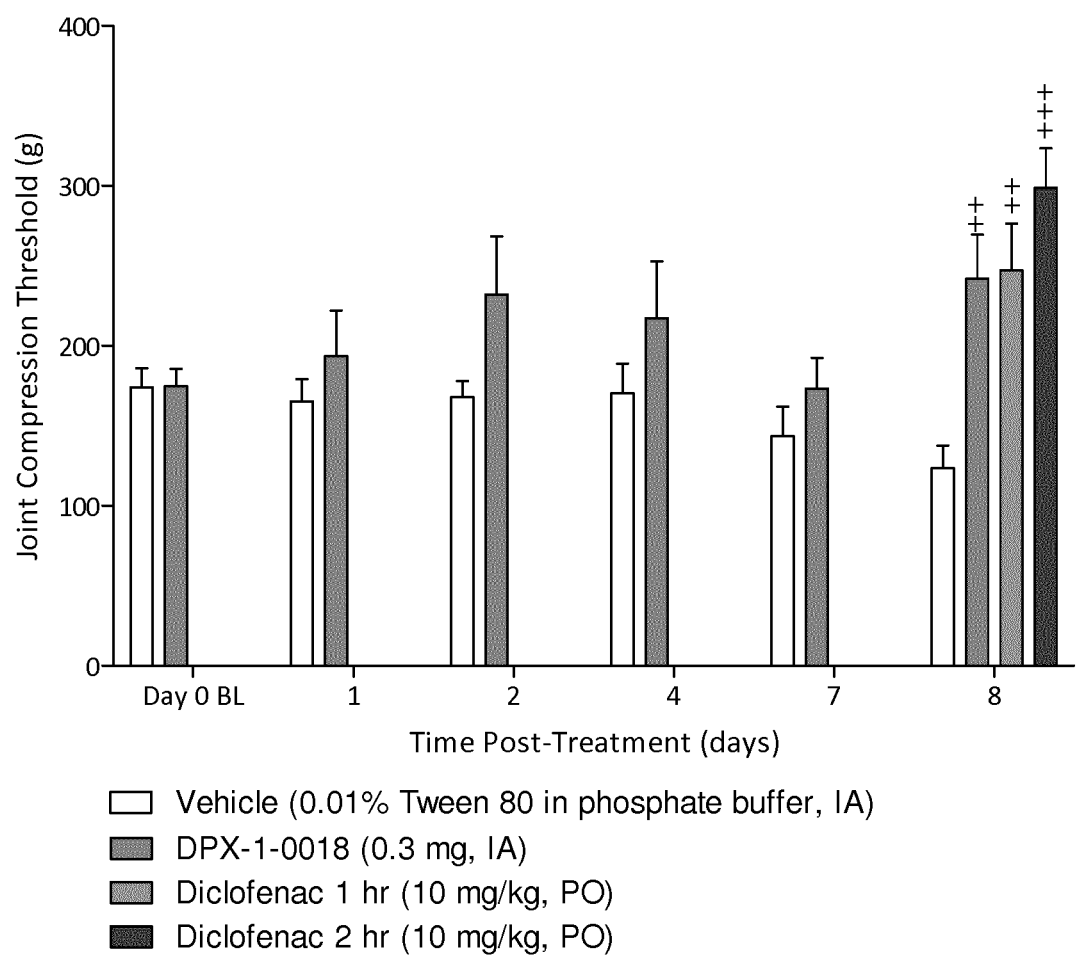
FIG. 4. Mean±SEM ipsilateral joint compression thresholds in vehicle, DPX-1-0018, or Diclofenac-treated animals during the pharmacological assessment period. All animals received an intra-articular injection of vehicle (0.01% Tween 80 in phosphate buffer) or DPX1-0018 (0.3 mg) on day 0, or Diclofenac via oral gavage on day 8 (n=10). ++/+++: $p<0.01/0.001$ vs. day 8 baseline value/vehicle.
Figure 5:
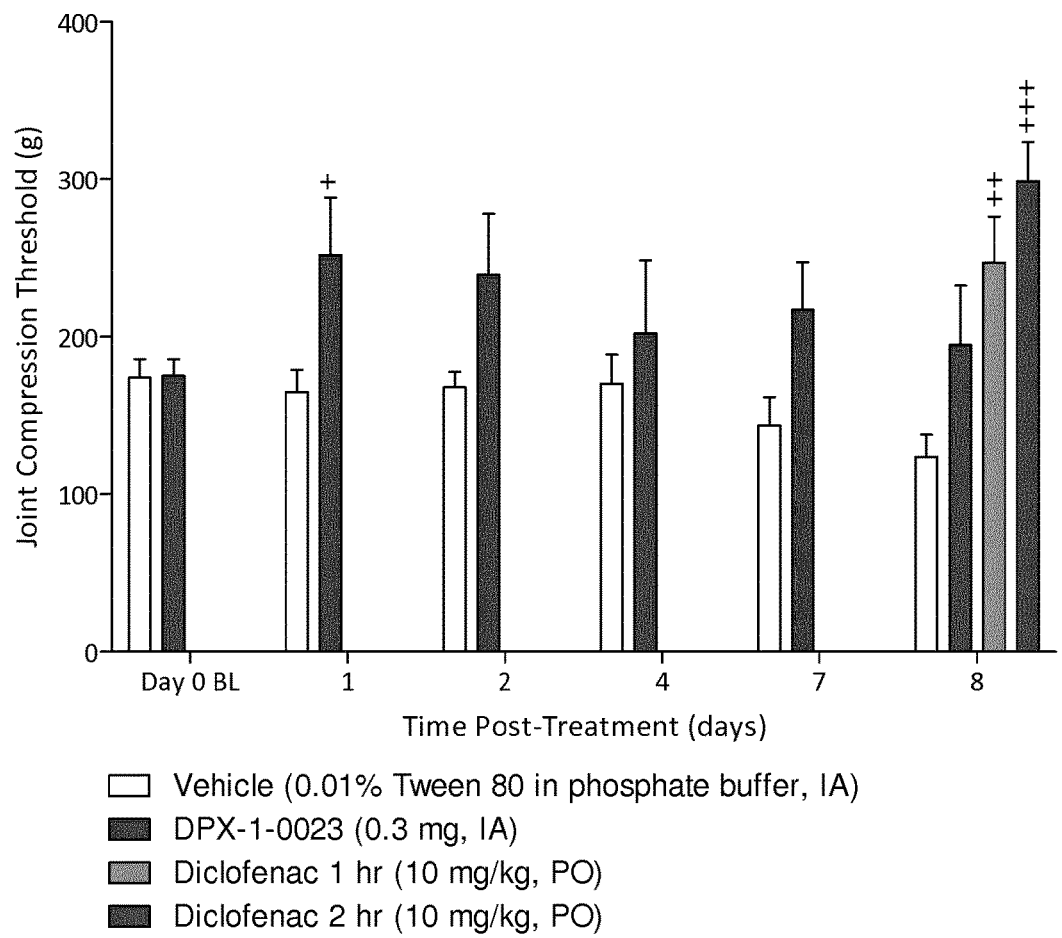
FIG. 5. Mean±SEM ipsilateral joint compression thresholds in vehicle, DPX-1-0023, or Diclofenac-treated animals during the pharmacological assessment period. All animals received an intra-articular injection of vehicle (0.01% Tween 80 in phosphate buffer) or DPX1-0023 suspension (0.3 mg) on day 0, or diclofenac via oral gavage on day 8 (n=10). +: $p<0.05$ vs. vehicle-treated animals; ++/+++: $p<0.01/0.001$ vs. day 8 baseline value.

A graphic presentation of the results is shown in FIGS. 4 and 5.

Conclusion

A single intra-articular administration of 0.3 mg test articles DPX-1-0018, or DPX-1-0023 significantly reversed osteoarthritis pain induced by a single injection of MIA compared to vehicle treated animals.

Example 4

Characterization of suspension for animal studies

The suspension was made by adding a known volume of a solution consisting of 0.01% Tween 80, 0.4% NaCl and 67 mM PBS pH 7.4 to a known amount of DPX-1-0023 to give a final prodrug concentration of 10 mg/mL (min 3.5 mL). This was then given 5×60 s ultrasound in a Covaris S2 with all parameters at max.

The resulting suspension was vortexed and 2×750 µL transferred by a 200-1000 µL pipette to a capped vial. The vial was closed with a Teflon coated rubber lid and sealed with an aluminum cap. This was done twice. One vial was used in animal studies and the other was used for characterizing the suspension.

Repetition of injections:

Method: After 20 s mixing on a Vortex mixer 30 µL suspension was withdrawn with a 27 G×20 mm injection needle equipped with a 100 µL Hamilton glass syringe and diluted to 10.00 mL with mobile phase. This was repeated 10 times.

8.3±0.4 mg/mL DPX-1-0023 was found.

Figure 6:
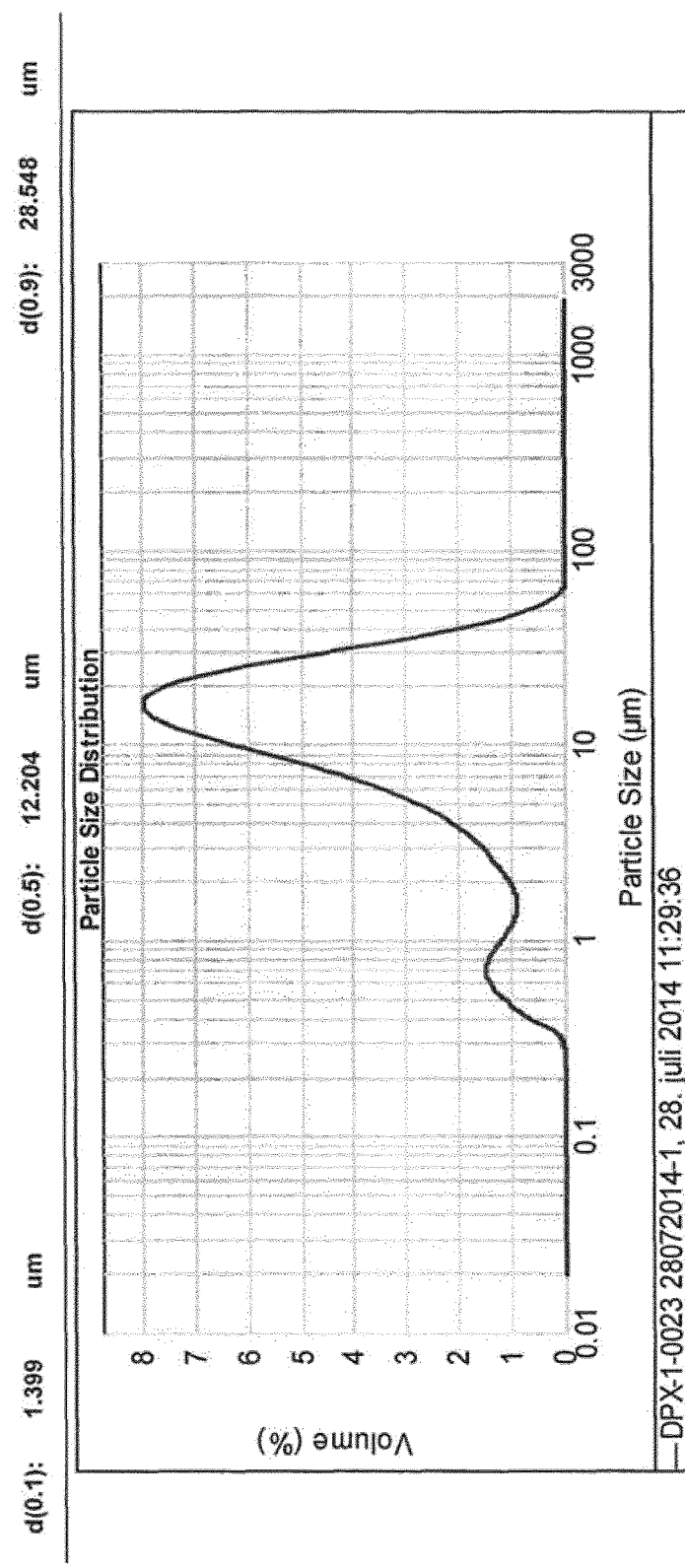
FIGS. 6 and 7. Particle size distribution of DPX-1-0023.
Figure 7:
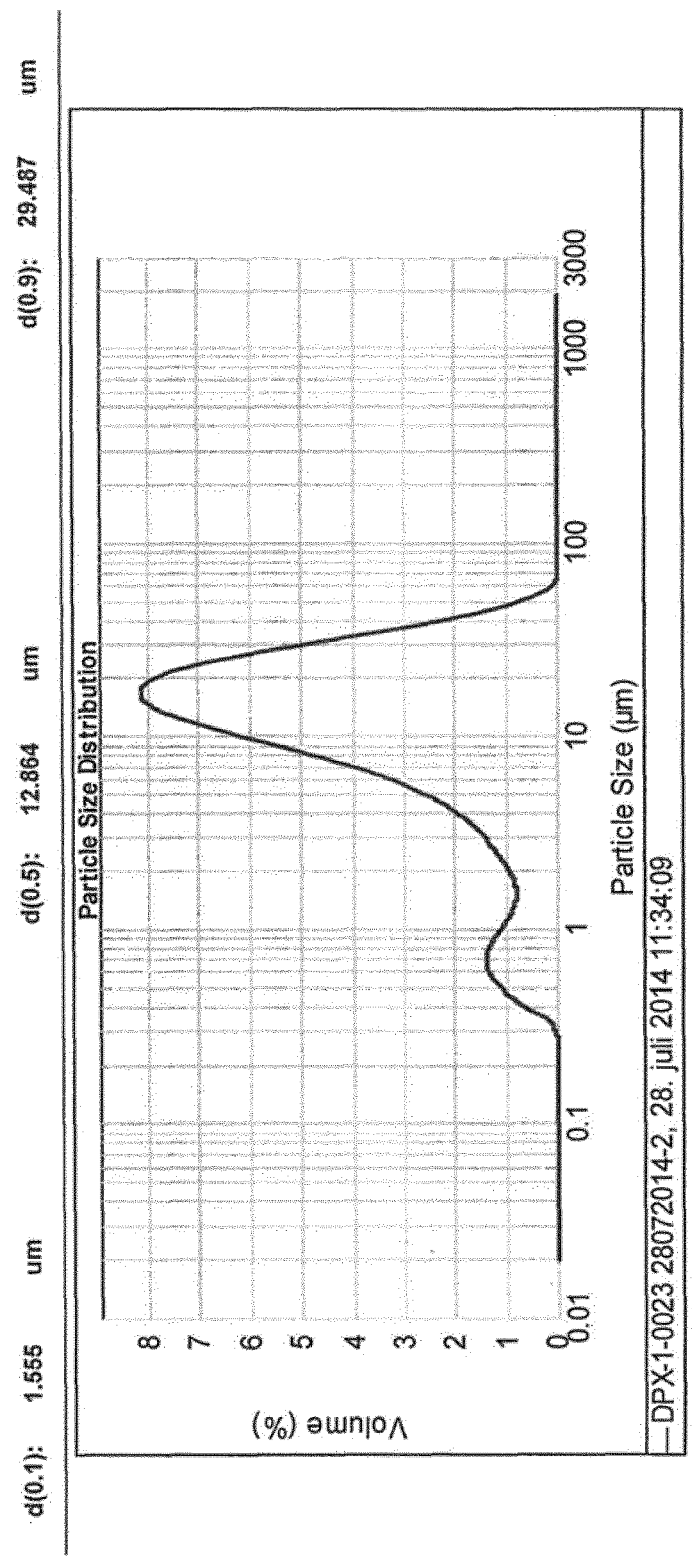

Particle size distribution:

Method: The particle size distribution was measured by laser diffraction with Malvern Mastersizer 2000 particle size analyzer using the Hydro 2000S wet sample dispersion unit (Malvern Instruments Ltd, Worcestershire, UK). After 20 s vortexing approximately 500 µL 10 mg mL$^{-1}$ suspension was added to 67 mM phosphate buffer pH 7.4 (120 mL) in the dispersion unit until the laser obscuration range was maintained between 2 and 5%. The suspension was stirred at 1015 rpm and a measurement time of 12 s applied. The results are shown in FIGS. 6 and 7.

Diclofenac content:

Method: 300 µL of the suspension (no vortexing) was centrifuged (5 min, 13.500 RPM, RT) and 2×100 µL of the supernatant was transferred to 200 µL mobile phase A, mixed and analyzed by HPLC.

Result:

3.6 µg/mL diclofenac was found in the suspension on the day of injection.

Example 5

Pharmaceutical composition-dispersion/suspension

The dispersion/suspension contains:

from about 2 to about 50 mg/ml of diclofenac prodrug,
sufficient isotonic adjusting substance to obtain an isotonic composition (eg glycerol or sodium chloride), eg from about 0.4 to about 0.9% w/v of sodium chloride,
optionally, from about 0.001 to about 0.1 mg/ml of a surfactant,
buffer solution pH 7.4.

A specific example is given in the following.

A suspension was made by adding a known volume of a solution consisting of 0.01% Tween 80, 0.4% NaCl and 67 mM PBS pH 7.4 to a known amount of DPX-1-0023 to give a final prodrug concentration of 10 mg/mL (min 3.5 mL). This was then given 5×60 s ultrasound in a Covaris S2 with all parameters at max.

The resulting suspension was vortexed and 2×750 µL transferred by a 200-1000 µL pipette to a capped vial. The vial was closed with a Teflon coated rubber lid and sealed with an aluminum cap. This was done twice. One vial was used in animal studies and the other was used for characterizing the suspension.

Example 6

Pharmaceutical Composition-in Solid Form to be Reconstituted with Aqueous Medium Before Application A well-defined amount of diclofenac prodrug, preferably in lyophilized form, is contained in a vial. The vial may also contain one or more solubilizers, one or more buffering agents, one or more pH adjusting agents and/or one or more isotonic adjusting agents.

Before administration an aqueous medium is added. The aqueous medium may have a pH value of from 1 to 4 in those cases where a solution is desired. The aqueous medium may contain one or more solubilizers, one or more buffering agents, one or more pH adjusting agents, one or more isotonic adjusting agents and/or one or more co-solvents. In the event the ready-to-use composition is a solution, The composition may also be provided in the form of a kit containing eg two vials, one containing lyophilized prodrug and the other containing an aqueous medium. Before administration the aqueous medium is added to the vial containing the lyophilized prodrug.

REFERENCES

Ref. 1: Reuben et al.

Reuben S. S., Connelly N. R. (1995) Postoperative analgesia for outpatient arthroscopic knee surgery with intraarticular bupivacaine and ketorolac. Anesth Analg 80: 1154-1157

Ref 2: Rasmussen et al.

Rasmussen S., Larsen A. S., Thomsen S. T., Kehlet H. (1998) Intra-articular glucocorticoid, bupivacaine and morphine reduces pain, inflammatory response and convalescence after arthroscopic meniscectomy. Pain 78: 131-134

Ref 3: R. Williams pKa Data Compiled by R. Williams (downloadable from http://research.chem.psu.edu/brpgroup/pKa_compilation.pdf)

Ref 4: Caballero et al.

Caballero et al. (2006) "Theoretical prediction of relative and absolute pKa values of aminopyridines", Biophysical Chemistry 124(2), p 155-160 (Ref. 3).

Ref 5: Drustrup et al.

Drustrup et al. (1991) "Utilization of prodrugs to enhance the transdermal absorption of morphine", International Journal of Pharmaceutics 71, 105-116

The invention claimed is:

1. A composition comprising:

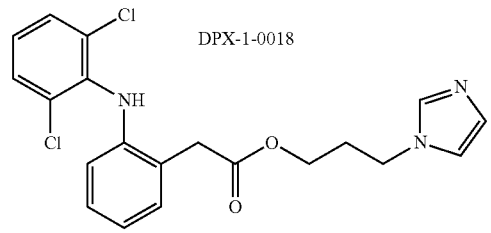

Chemical Formula: $C_{20}H_{19}Cl_2N_3O_2$
Molecular Weight: 404,29 or a salt, solvate or hydrate, thereof.

2. A composition comprising:

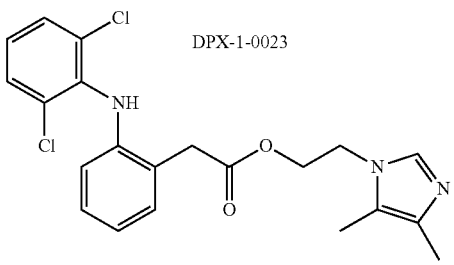

Chemical Formula: $C_{21}H_{21}Cl_2N_3O_2$
Molecular Weight: 418,32 or a salt, solvate or hydrate, thereof.

3. The composition according to claim 1, further comprising at least one pharmaceutically acceptable carrier, vehicle and/or adjuvant.

4. The composition according to claim 3, wherein the composition is suitable for intra-articular injection.

5. The composition according to claim 2, further comprising at least one pharmaceutically acceptable carrier, vehicle and/or adjuvant.

6. The composition according to claim 5, wherein the composition is suitable for intra-articular injection.

7. A method of treating pain and/or inflammation in a joint, comprising:
  injecting into the synovial fluid of the joint a solution having a pH of 6 or less and comprising a dissolved compound selected from the group consisting of:

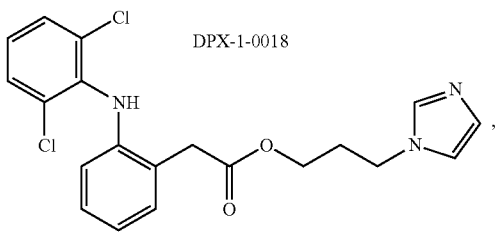

Chemical Formula: $C_{20}H_{19}Cl_2N_3O_2$
Molecular Weight: 404,29

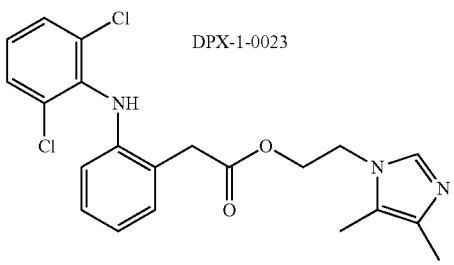

Chemical Formula: $C_{21}H_{21}Cl_2N_3O_2$
Molecular Weight: 418,32 and salts, solvates or hydrates thereof; and
  forming a precipitate of the compound in the joint.

8. The method of claim 7, wherein the pain and/or inflammation in the joint is postoperative pain following arthroscopic surgery.

9. The method of claim 7, wherein the solution further comprises a local anesthetic agent.

10. The method of claim 9, wherein the local anesthetic agent is selected from the group consisting of: amethocaine, chlorprocaine, etidocaine, lidocaine, bupivacaine, mepivacaine, prilocaine, ropivacaine, and procaine.

11. The method of claim 7, wherein the solution further comprises an opiod or an analgesic agent.

12. The method of claim 11, wherein the opiod or strong analgesic agent is selected from the group consisting of: alfentanil, alphaprodine, anileridine, buprenorphine, buturphenol, codeine, dextromoramide, dextroproxyphene, dihydrocodeine, fentanyl, dydrocodone, hydromorphone, ketobemidone, meptazinol, methadone, morphine, oxycodone, oxymorphone, pentazocine, pethidine, phenazocine, phenoperidine, and sulfentanil.

13. The method of claim 7, wherein the compound has the following structure

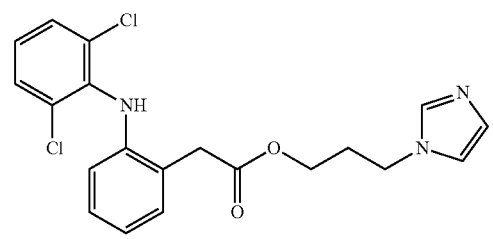

Chemical Formula : $C_{20}H_{19}Cl_2N_3O_2$
Molecular Weight: 404.29 or a salt, solvate or hydrate, thereof.

14. The method of claim 7, wherein the compound has the following structure

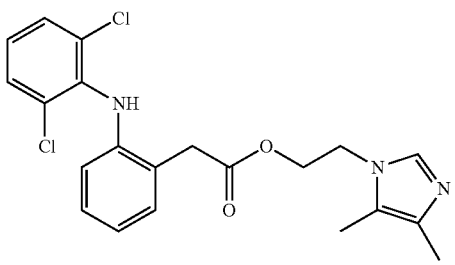

Chemical Formula : $C_{21}H_{21}Cl_2N_3O_2$
Molecular Weight: 418.32 or a salt, solvate or hydrate, thereof.

* * * * *